United States Patent [19]
Rush et al.

[11] Patent Number: 4,777,937
[45] Date of Patent: Oct. 18, 1988

[54] MOOD ALTERING DEVICE

[75] Inventors: Charles Rush; Peter J. Guinan, both of Woodstock, N.Y.

[73] Assignee: Tranquil Times, Inc., Woodstock, N.Y.

[21] Appl. No.: 760,487

[22] Filed: Jul. 30, 1985

[51] Int. Cl.$^4$ ............................................. A61M 21/00
[52] U.S. Cl. ........................................................ 600/27
[58] Field of Search ................. 128/1 C, 1 R, 745–746

[56] References Cited

U.S. PATENT DOCUMENTS

| | | | |
|---|---|---|---|
| 2,843,111 | 7/1958 | Roll | 128/1 C |
| 3,722,501 | 3/1973 | Derouineau | 128/1 C |
| 3,773,049 | 11/1973 | Rabichev et al. | 128/1 C X |
| 4,191,175 | 3/1980 | Nagle | 128/1 C |
| 4,289,121 | 9/1981 | Kupriyanovich | 128/1 C |
| 4,315,502 | 2/1982 | Gorges | 128/1 C |
| 4,335,710 | 6/1982 | Williamson | 128/1 C |
| 4,388,918 | 6/1983 | Filley | 128/1 C |
| 4,553,534 | 11/1985 | Stiegler | 128/1 R X |

OTHER PUBLICATIONS

New Tools and Techniques for Brain Growth and Mind Expansion–Mega Brain, by Michael Hutchison, published by Beech Tree Books, William Morrow and Company, Inc., 105 Madison Avenue, New York, NY 10016, Chapter 15, "Gazing Hard Into the Void: Tranquilite", pp. 261–263–copyright 1986.

"Psychology of Consciousness", Robert E. Orenstein, Pelican Books, 1975, pp. 142, 143.

*Primary Examiner*—William E. Kamm
*Assistant Examiner*—Angela D. Sykes
*Attorney, Agent, or Firm*—Auslander & Thomas

[57] ABSTRACT

The invention features a method and apparatus for altering the mood of an individual. A facial mask is provided that excludes external stimuli while providing visual and auditory stimulation designed to influence the brain wave pattern.

The visual stimulus introduces a continuous, uniform light of a particular color. The light stimulus is designed to produce an effect known as ganzfeld, wherein there occurs a complete loss of visual sensation.

10 Claims, 1 Drawing Sheet

MOOD ALTERING DEVICE

This invention relates to a mood altering device, and more particularly, to a mood altering device that utilizes visual and auditory stimulation to achieve relaxation and reduction of stress.

BACKGROUND OF THE INVENTION

In recent times, the medical and dental professions have been investigating the possibilities of treating patients using light and sound therapy.

It is becoming apparent that both light and sound can effect the brain wave patterns in human beings. Light therapy is being tried as a means to prevent and reduce depression in certain individuals.

Some dentists are using white noise to control a patient's fear of dentistry and to reduce pain.

The present invention contemplates the use of a particular type of visual and auditory stimulation for treating stress and for enhancing the mood of relaxation in various individuals.

The party to be treated is directed to wear a facial mask that introduces a continuous light of a glowing uniform color to the sight. Simultaneously therewith, a gentle rhythmic pink noise is introduced to the hearing. The pink noise is simulative of the sound of flowing water.

The uniform color is produced by an electroluminescent light generator. The facial mask shields the individual from external stimuli, while providing the light and sound stimulation.

The continuous uniform glowing color soon produces an effect known as ganzfeld. Ganzfeld is a condition in which the subject loses all sense of visual externality, i.e., a complete loss of the sensation of seeing occurs wherein the individual does not even know whether his eyes are open or closed. There is not merely an inability to see, but rather, there is a complete blanking out of fisual sensation. The ganzfeld effect combined with the monotonous rhythmic sound produces a powerful mood alteration in the individual. Stress is quickly reduced and the individual becomes relaxed and serene.

DISCUSSION OF RELATED ART

In U.S. Pat. No. 4,315,502, issued Feb. 16, 1985, a relaxation device is shown wherein both visual and auditory stimulation is introduced to the sight and hearing. The stimulation has as its purpose to produce relaxation. Both the light and auditory inputs are pulsed are are caused to be in synchronism with each other. The stimulative inputs are introduced by means of an eye mask and a pair of head phones.

The light and sound pluses are used to effect the brain wave pattern.

BRIEF SUMMARY OF THE INVENTION

The present invention differs from the aforementioned patented relaxation device in U.S. Pat. No. 4,315,502, in that the light stimulation is continuous instead of pulsating. The continuous light is desired to product ganzfeld, a visual "blanking out", which in turn affects the brain waves. While both light and sound are simultaneously introduced, the rhythmic pink noise is not synchronously coupled to the light generator, i.e., the two stimulative effects are independent of each other.

The invention features a method and apparatus for altering the mood of an individual.

The individual is simultaneously subjected to light and sound stimulation, which affects the brain waves and induces a feeling of relaxation.

The light stimulation is introduced to the sight of the individual in a face mask that excludes external light stimulation.

The introduced light is of a substantially continuous and uniform color, which is designed to produce a condition or effect known as ganzfeld, wherein there is a loss of visual sensation.

A rhythmic pink noise is simultaneously introduced to the hearing of the subject. The pink noise is a monotonous sound simulative of flowing water. The combined effect of both the light and sound stimulation reduces stress and provides a state of relaxation.

The light is produced by an electroluminescent light generator and has a glowing appearance.

The light color can be selected to enhance a particular mood. For example, blue or green is most useful for inducing relaxation.

It is an object of this invention to provide an improved mood altering method and device.

It is another object of the invention to provide an apparatus that provides visual stimulation for inducing a ganzfeld effect.

Although such novel feature or features believed to be characteristic of the invention are pointed out in the claims, the invention and the manner in which it may be carried out, may be further understood by reference to the description following and the accompanying drawing.

DETAILED DESCRIPTION OF THE INVENTION

Referring now to the figures in greater detail, where like reference numbers denote like parts in the various figures.

Generally speaking, the invention relates to a mood altering method and apparatus. The method and device features both light and sound stimulation designed to influence the brain waves and induce a feeling of relaxation.

Figure 1:
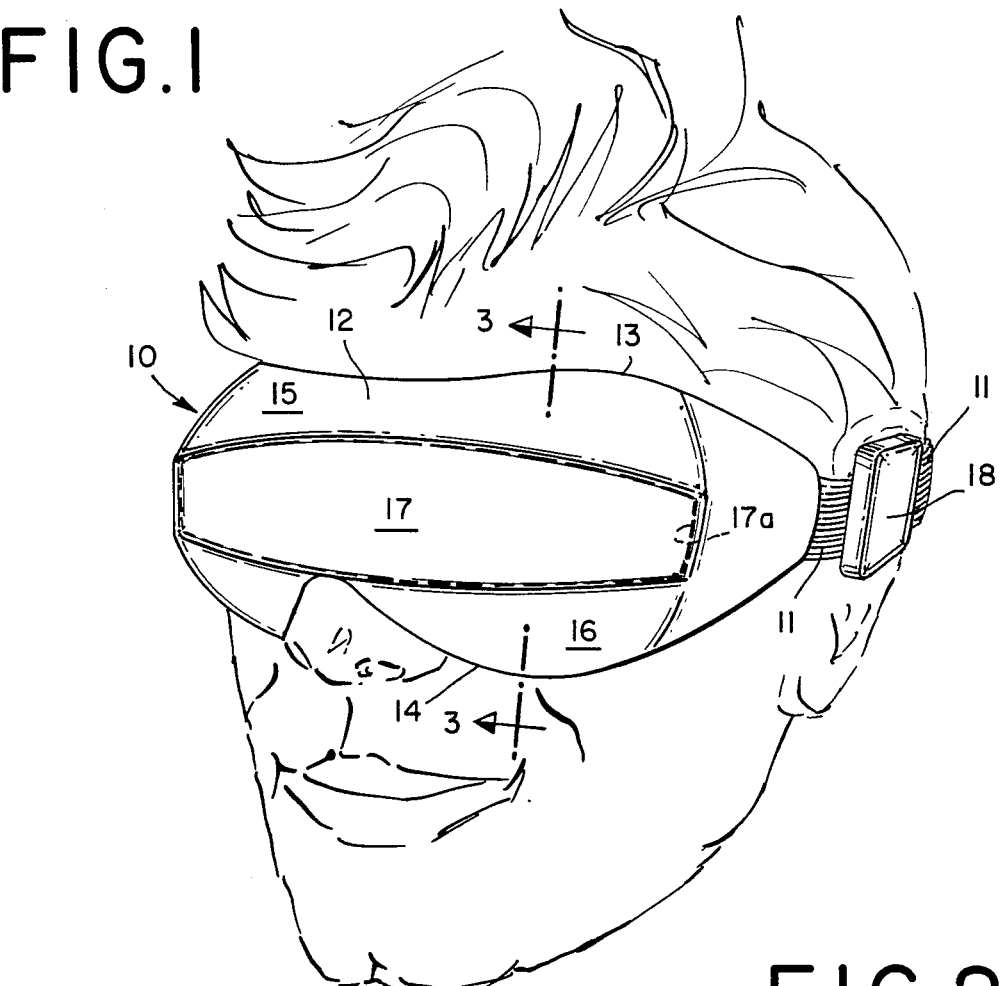
FIG. 1 is a perspective in situ view of the face mask of this invention upon the head of a user.
Figures 2, 3:
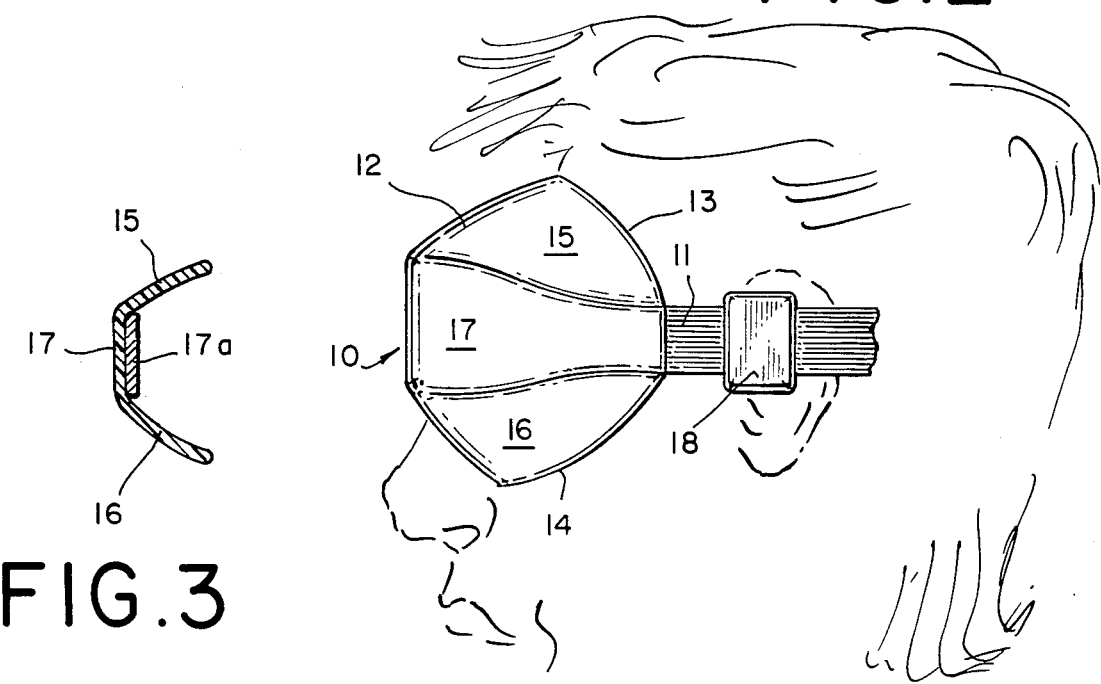
FIG. 2 is an insitu side view of the invention shown in FIG. 1.
FIG. 3 is a sectional view taken along line 3—3 of FIG. 1.

Now, referring to FIGS. 1 and 2, a face mask 10 of the invention is illustrated. The face mask 10 comprises a generally elastic head band 11 and an eye shield 12. The elastic head band 11 draws the eye shield 12 into a snug, conforming contact with the face of the user. The eye shield 12 comprises a conforming facial surfaces 13 and 14, in order to shield the user's eyes from external light stimulation.

The eye shield comprises the top and bottom opaque sections 15 and 16, respectively, and an opaque section 17 containing an internally disposed electroluminescent strip 17a. The electroluminescent strip 17a (best seen in FIG. 3) comprises a broad band of liquid crystal or phosphorescent material that completely encompasses the eye field of the mask wearer. The liquid crystal or phosphorescent material is caused to glow, i.e., emit light, by means of a light-generating circuit (not shown). The electroluminescent strip 17a is manufactured by Luminescent Systems, Inc., Etna Road, Lebanon, N.H. 03766, Model Nos. 0431-4, 0554 and 0555.

The mask 10 also contains a pair of earphones 18 that are designed to fit over the ears and introduce a rhythmic pink noise (filtered white noise).

The circuitry for the visual stimulation comprises a video driver circuit which boosts 6 volt battery current, using transistor logic circuit No. U6 TLC 555, to 110 volt alternating current to activate the liquid crystal display strip 17a. The circuit is available from Measurement Specialties, Inc., 20 Campus Road, Totawa, N.J. 07512. The pink noise generating circuit is also available from Measurement Specialties, Inc. The above circuits have a drawing No. MSI-013.

Pink noise stimulation is similar to the white noise generation (filtered white noise) currently being used in the dental field to suppress pain and anxiety in dental patients. The pink noise comprises a rhythmic, monotonous sound similar to that of flowing or gurgling water. This rhythmic sound tends to induce a feeling of drowsiness and relaxation.

The electroluminescent strip 17a provides a continuous, uniform color input, which visual input is designed to provide a ganzfeld effect. The wearer experiences a loss of visual sensation, such that he is not aware whether his eyes are open or shut.

Both the visual and auditory stimulation provided by mask 10 affects the brain waves of the wearer.

Several different strips 17a can be simultaneously disposed within opaque section 17 to provide different colors.

A selector panel (not shown) provides various light and sound controls, such that a particular color can be selected for a visual input from one of the strips 17a. Different colors can effect different moods. Blue or green is most useful in effecting relaxation and stress relief.

Light and sound intensity is also controllable by the panel.

Conforming strips 15 and 16 of the face mask 10 can be lined along edges 13 and 14, respectively, with foam padding or cushioning to provide comfort to the wearer.

The face mask 10 can be made from plastic or other suitable materials consistent with the general purposes set forth herein.

Ther terms and expressions which are employed are used as terms of description; it is recognized, though, that various modifications are possible.

It is also understood the following claims are intended to cover all of the generic and specific features of the invention herein described, and all statements of the scope of the invention which, as a matter of language, might fall therebetween.

Having described certain forms of the invention in some detail, what is claimed is:

1. A mood altering device adapted to cause the user to have a loss of the sense of visual externality and experience a sense of relaxation, comprising a facial mask adapted to fit over the eyes forming an opaque shield adapted to completely cover the eyes against entry of outside light, said facial mask including electroluminescent strip means in said shield adapted to glow, said electroluminescent strip means adapted to provide a substantially continuous unvarying light of substantially uniform color, said light adapted to induce a hypnotic-like ganzfeld effect, and auditory stimulation means adapted to provide pink noise.

2. The invention of claim 1 wherein said pink noise is a substantially continuous, monotonous sound simulating the sound of flowing water.

3. The invention of claim 1 whereinn said facial mask further includes integral stimulation means adapted to provide pink noise.

4. The invention of claim 1 wherein said shield is a single shield shielding both eyes.

5. The invention of claim 4 including a single glowing strip.

6. The invention of claim 4 including a plurality of selectable electroluminescent strips in said shield each adapted to glow in a selected color.

7. The invention of claim 1 including a plurality of selectable electroluminescent strips in said shield each adapted to glow in a selected color.

8. A method of altering the mood of an individual adapted to cause a loss of the sense of visual externality and experience a sense of relaxation, comprising the steps of providing sheilding to eyes from all external light, providing an electroluminescent glow of substantially continuous unvarying light of substantially uniform color, said light adapted to induce a hypnotic-like ganzfeld effect, and providing auditory stimulation means adapted to provide pink noise.

9. The invention of claim 8 wherein said provided pink noise is a substantially continuous, monotonous sound simulating the sound of flowing water.

10. The invention of claim 8 including the step of providing glow in a selected color.

* * * * *